United States Patent [19]

Umemoto et al.

[11] Patent Number: 4,973,697
[45] Date of Patent: Nov. 27, 1990

[54] 2-HALOPYRIDINE-6-SULFONIC ACID AND ITS SALT

[75] Inventors: Teruo Umemoto; Kikuko Harasawa, both of Sagamihara, Japan

[73] Assignees: Onoda Cement Co., Ltd., Ondoda; Sagami Chemical Research Center, Tokyo, both of Japan

[21] Appl. No.: 505,455

[22] Filed: Apr. 6, 1990

[30] Foreign Application Priority Data

Apr. 18, 1989 [JP] Japan ................................. 64-96322

[51] Int. Cl.$^5$ ........................................... C07D 213/71
[52] U.S. Cl. ................................................. 546/295
[58] Field of Search ....................................... 546/295

[56] References Cited

FOREIGN PATENT DOCUMENTS

WO98/06230 7/1989 PCT Int'l Appl. ................. 546/295

OTHER PUBLICATIONS

Hertog et al., Chemical Abstracts, vol. 53, Entry 10203(d), 1959.

*Primary Examiner*—Mary C. Lee
*Assistant Examiner*—Lenora Mitenberger
*Attorney, Agent, or Firm*—Oblon, Spivak, McClelland, Maier & Neustadt

[57] ABSTRACT

A 2-halopyridine-6-sulfonic acid and its salt represented by the formula:

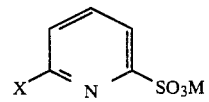

wherein X is a halogen atom, and M is a hydrogen atom or a metal atom. The compounds are useful as intermediates for producing fluorinating agents (reagents for introducing fluorine atoms).

6 Claims, No Drawings

2-HALOPYRIDINE-6-SULFONIC ACID AND ITS SALT

The present invention relates to a novel 2-halopyridine-6-sulfonic acid and its salt, which are useful intermediates for producing N-fluoro-2-halopyridinium-6-sulfonates useful as fluorinating agents (reagents for introducing fluorine atoms).

The present inventors have previously reported on an N-fluoropyridinium triflate having an electron attracting group such as a chlorine atom on the pyridine ring, as an excellent reagent for fluorinating a phenol as one of aromatic compounds under a mild condition (Tetrahedron Lett., 27, 4465 (1986)). However, since then, it has been found that when such a fluorinating agent is employed, a practical difficulty will be brought about in the post treatment process. For example, when phenol is fluorinated with N-fluoro-3,5-dichloropyridinium triflate, not only the fluorinated phenol, but also equivalent amounts of 3,5-dichloropyridine and trifluoromethanesulfonic acid will be formed, as shown by the following formula:

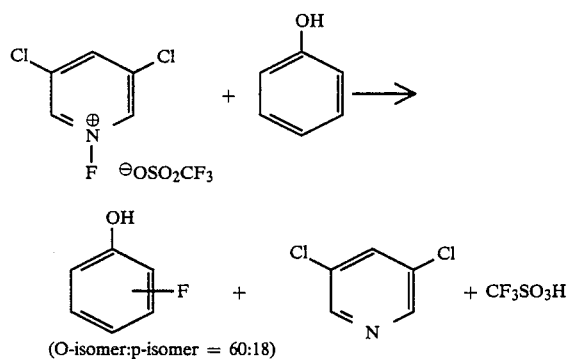

(O-isomer:p-isomer = 60:18)

The latter trifluoromethanesulfonic acid can readily be removed by washing the reaction mixture with water. However, the former 3,5-dichloropyridine is not soluble in an acidic aqueous solution and therefore can not easily be separated by the step of washing with water. Its separation requires a cumbersome process. Therefore, such a conventional technique had a serious drawback.

The present inventors have conducted extensive studies to solve such a problem with an idea of incorporating a water-soluble functional group into the pyridine backbone. As a result, the object has been accomplished by incorporating an electron attracting halogen atom at the 2-position of the pyridine nucleus on one hand and incorporating a water-soluble sulfonic acid group at the 6-position on the other hand, and the present invention has been thereby accomplished.

The present invention thus provides a 2-halopyridine-6-sulfonic acid and its salt represented by the formula:

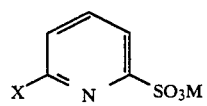

(I)

wherein X is a halogen atom, and M is a hydrogen atom or a metal atom.

The 2-halopyridine-6-sulfonic acid and its salt represented by the formula I are intermediates useful for the production of N-fluoro-2-halopyridinium-6-sulfonates which are useful as fluorinating agents (see Reference Examples 1 and 2 given hereinafter). The N-fluoro-2-halopyridinium-6-sulfonates are useful particularly as reagents for fluorinating aromatic compounds. Such N-fluoro-2-halopyridinium-6-sulfonates can be synthesized in one step from the compounds of the present invention, and they are useful as fluorinating agents which solve the above-mentioned problem (see Reference Examples 1 to 5 given hereinafter). Namely, when such a fluorinating agent is used for fluorinating an aromatic compound, the 2-halopyridine-6-sulfonic acid derived from the fluorinating agent as shown by the following reaction formula, is water-soluble and therefore can readily be separated from the fluorinated aromatic compound by the step of washing with water.

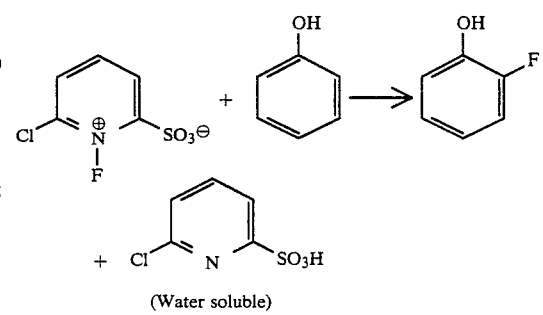

(Water soluble)

Further, a fluorinating agent produced from the compound of the present invention has a characteristic which is extremely useful from the viewpoint of synthetic chemistry in that it produces an ortho-isomer only or an ortho-isomer with a remarkably high reaction selectivity in the fluorination of phenol or phenylurethane (see Reference Examples 3 to 5 given hereinafter).

Now, the present invention will be described in detail with reference to the preferred embodiments.

The compound of the present invention represented by the above-formula I, can be prepared by reacting a metal salt of sulfurous acid to a 2,6-dihalopyridine of the formula:

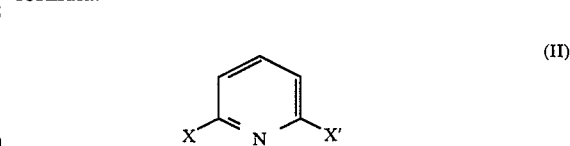

(II)

wherein X and X' are the same or different halogen atoms, and if necessary, treating the product with an acid.

The 2,6-dihalopyridine of the formula II is a compound which is readily available on an industrial scale. For example, it includes 2,6-difluoropyridine, 2,6-dichloropyridine, 2,6-dibromopyridine, 2,6diiodopyridine and 2,6-chlorofluoropyridine. The metal salt of sulfurous acid is also readily available on an industrial scale, and it includes lithium sulfite, sodium sulfite, potassium sulfite, magnesium sulfite, calcium sulfite and barium sulfite.

The reaction is conducted preferably in a solvent such as water, methanol, ethanol or a solvent mixture thereof. The reaction temperature is required to be at least 80° C. The temperature is preferably from 100° C. to 200° C. so that the reaction proceeds in good yield.

Further, a metal salt of the 2-halopyridine-6-sulfonic acid represented by the formula I may readily be produced by treating a 2-halopyridine-6-sulfonic acid with a metal hydroxide (see Example 4).

Now, the present invention will be described in further detail with reference to Examples and Reference Examples. However, it should be understood that the present invention is by no means restricted by such specific Examples.

EXAMPLE 1

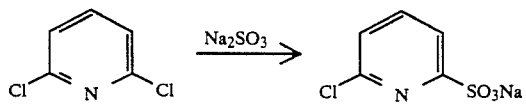

Into a 50 ml autoclave, 2.22 g (15 mmol) of 2,6-dichloropyridine and 4.5 ml of ethanol were introduced and dissolved. To the solution, 2.27 g (18 mmol) of sodium sulfite dissolved in 18 ml of water, was added, and after sealing, the mixture was heated in an oil bath of 170° C. for 12 hours. After completion of the reaction, the mixture was cooled, and after an addition of 30 ml of water, extracted with methylene chloride (30 ml×3 times). The aqueous layer was distilled under reduced pressure, and 200 ml of ethanol was added. The mixture was heated. After filtering off insoluble precipitates, the filtrate was distilled under reduced pressure to obtain 0.94 g (30%) of sodium 2-chloropyridine-6-sulfonate as crystalline solid. Purification was conducted by recrystallization from ethanol. The physical property values are shown below.

Melting point: 292°–294° C.

$^1$H-NMR (In heavy dimethylsulfoxide): 7.47 ppm (1H,d,J=7.7 Hz), 7.88 ppm (1H,d.d,J=7.7Hz,7.7 Hz), 7.71 ppm (1H,d,J=7.7 Hz).

IR (KBr disk): 3475, 1570, 1420, 1200, 1150, 1060, 1040, 800, 670, 630, 620 cm$^{-1}$.

Mass: 64 ($SO_2^+$).

Elemental analysis: $C_5H_3NClSO_3Na$: Found: C,27.65; H,1.39; N,6.25%; Calculated: C,27.85; H,1.40; N,6.50%.

EXAMPLE 2

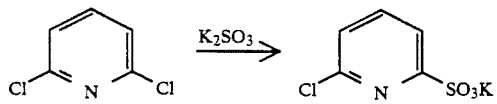

In the same manner as in Example 1, 2,6-dichloropyridine and potassium sulfite were reacted to obtain 540 mg (15.8%) of potassium 2-chloropyridine-6-sulfonate. Purification was conducted by recrystallization from ethanol.

Melting point: 240°–243° C.

$^1$H-NMR (In heavy dimethylsulfoxide): 7.45 ppm (1H,d.d,J=8 Hz,2 Hz), 7.88 ppm (1H,d.d,J=8 Hz,8 Hz), 7.72 ppm (1H,d.d,J=8 Hz,2 Hz).

IR (KBr disk): 3475, 1580, 1560, 1425, 1400, 1220, 1160, 1050, 800, 675, 630 cm$^{-1}$.

Mass: 112 (M$^+$-$SO_3K$), 64 ($SO_2^+$).

Elemental analysis: $C_5H_3NClSO_3K$: Found: C,25.88; H,1.26; N,6.01%; Calculated: C,25.92; H,1.31; N,6.05%.

EXAMPLE 3

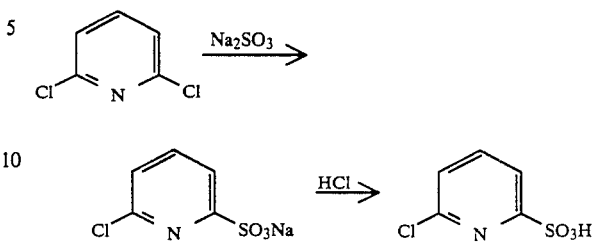

Into 0.82 g (3.8 mmol) of sodium 2-chloropyridine-6-sulfonate prepared in accordance with Example 1, 10 ml of concentrated hydrochloric acid was added, and the mixture was stirred at room temperature overnight. Then, the solvent was distilled off, and after an addition of 200 ml of 2-propanol, the residue was heated. Insoluble matters were removed by filtration, and the filtrate was distilled under reduced pressure to obtain 710 mg (96.6%) of 2-chloropyridine-6-sulfonic acid as crystalline solid. Purification was conducted by recrystallization from 2-propanol.

Melting point: 274°–275° C.

$^1$H-NMR (In heavy dimethylsulfoxide): 7.46 ppm (1H,d.d,J=7.56 Hz,0.85 Hz), 7.87 ppm (1H,d.d,J=7.56 Hz,7.90 Hz), 7.71 ppm (1H,d.d,J=7.90 Hz,0.85 Hz).

IR (KBr disk): 3100, 1600, 1510, 1420, 1290, 1270, 1235, 1170, 1050, 815, 665, 615, 510 cm$^{-1}$.

Mass: 193 (M$^+$), 112 (M$^+$-$SO_3H$).

Elemental analysis: $C_5H_4NClSO_3$: Found: C,31.08; H,2.16; N,7.28%; Calculated: C,31.02; H,2.08; N,7.23%.

EXAMPLE 4

Into a 200 ml egg-plant type flask, 785.2 mg (4.06 mmol) of 2-chloropyridine-6-sulfonic acid was charged, then dissolved with an addition of 2 ml of water and neutralized with an aqueous lithium hydroxide solution. The solvent was distilled off under reduced pressure, and after an addition of 100 ml of 2-propanol, the mixture was heated. Insoluble matters were removed by filtration, and the solvent was distilled under reduced pressure to obtain 725 mg (89.5%) of lithium 2-chloropyridine-6-sulfonate as crystalline solid. Purification was conducted by recrystallization from 2-propanol.

Melting point: More than 300° C.

$^1$H-NMR (In heavy dimethylsulfoxide): 7.44 ppm (1H,d.d,J=7.0 Hz, 1.5 Hz), 7.71 ppm (1H,d.d,J=7.0 Hz, 1.5 Hz), 7.88 ppm (1H,d.d,J=7.0 Hz, 7.0 Hz).

IR (KBr disk): 3550, 3475, 1580, 1430, 1220, 1160, 1050, 1000, 800, 680, 630, 510 cm$^{-1}$.

Mass: 64 ($SO_2^+$),7 (Li$^+$).

Elemental analysis: $C_5H_4NClSO_3Li$: Found: C,30.11; H,1.51; N,7.06%; Calculated: C,30.09; H,1.52; N,7.02%.

EXAMPLE 5

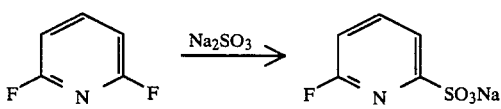

In the same manner as in Example 1, 1.725 g (15 mmol) of 2,6-difluoropyridine and 2.27 g (18 mmol) of sodium sulfite were reacted at 170° C. for 5 hours. By conducting the same post-treatment as in Example 1, 0.315 g (10.5%) of sodium 2-fluoropyridine-6-sulfonate was obtained.

Melting point: 267°-269° C. (2-propanol)

$^1$H-NMR (In heavy dimethylsulfoxide): 7.12 ppm (1H,d.d.d,J=8.2 Hz,2.82 Hz,0.62 Hz), 7.66 ppm (1H,d.d.d,J=7.48 Hz,2.5 Hz,0.74 Hz), 7.99 ppm (1H,d.d.d,J=7.50 Hz, 7.50 Hz,7.81 Hz).

$^{19}$F-NMR (In heavy dimethylsulfoxide): 68.3 ppm (d,J=7.0 Hz).

IR (KBr disk): 3500, 3100, 1600, 1580, 1440, 1230, 1210, 1150, 1060, 995, 905, 810, 705, 625, 535 cm$^{-1}$.

Mass: 64 (SO$_2$$^+$).

Elemental analysis: C$_5$H$_3$NFSO$_3$Na: Found: C,30.08; H,1.78; N,6.85%; Calculated: C,30.16; H,1.52; N,7.04%.

REFERENCE EXAMPLE 1

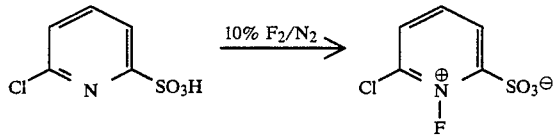

Into a 25 ml egg-plant type flask equipped with a gas supply tube, 209 mg (1.08 mmol) of 2-chloropyridine-6-sulfonic acid, 0.1 ml of water and 2 ml of acetonitrile were charged, and the flask was immersed in an acetone bath of −25° C. After flushing with nitrogen, a gas mixture of 10% F$_2$/N$_2$ was blown into this solution in an amount of 3 equivalent at a flow rate of 30 ml/min under stirring. 25 ml of tetrahydrofuran was added thereto and stirred to return the temperature to room temperature. Crystals were collected by filtration and sufficiently dried under reduced pressure to obtain 176.7 mg (77.4%) of N-fluoro-2-chloropyridinium-6-sulfonate as crystals. Purification was conducted by recrystallization from acetonitrile. The physical property values are shown below.

Melting point: 171°-173° C.

$^1$H-NMR (In heavy acetonitrile): 8.54 ppm (1H,d.d,J=8.0 Hz,8.0 Hz), 8.38 ppm (1H,d.d.d,J=8.0 Hz,8.0 Hz,2.0 Hz), 8.21 ppm (1H,d.d.d,J=8.0 Hz,8.0 Hz,2.0 Hz).

$^{19}$F-NMR (In heavy acetonitrile): −30.6 ppm (NF,s).

IR (On NaCl plate, Nujol): 3100, 2950, 2850, 1570, 1280, 1250, 1150, 810 cm$^{-1}$.

Mass: 112 (M$^+$—F,SO$_3$).

Elemental analysis: C$_5$H$_3$NClFSO$_3$: Found: C,28.31; H,1.44; N,6.57%; Calculated: C,28.38; H,1.43; N,6.62%.

REFERENCE EXAMPLE 2

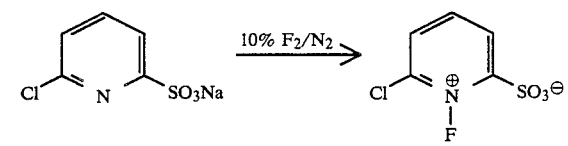

Into a 100 ml egg-plant type flask equipped with a gas supply tube, 200 mg (0.93 mmol) of sodium 2-chloropyridine-6-sulfonate and 50 ml of dry acetonitrile were charged and flushed with nitrogen. The flask was immersed in an acetone bath cooled to −40° C., a gas mixture of 10% F$_2$/N$_2$ was blown into the mixture in an amount of 10 equivalent at a rate of 30 ml/min under stirring. After completion of the reaction, the flask was flushed with nitrogen, and the mixture was returned to room temperature and filtered with celite. The filtrate was concentrated under reduced pressure, whereby crystals precipitated. The crystals were recrystallized from acetonitrile-ethyl ether to obtain 98.5 mg (50.1%) of N-fluoro-2-chloropyridinium-6-sulfonate. The physical property values are shown in Reference Example 1.

REFERENCE EXAMPLE 3

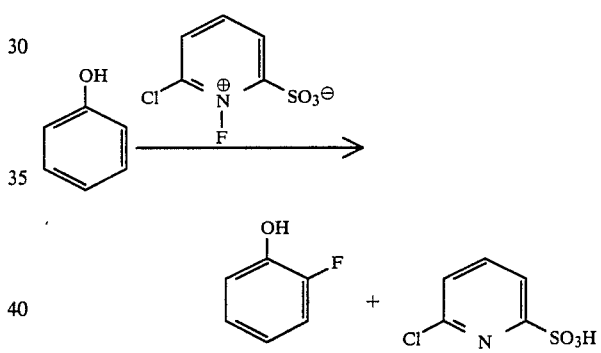

A 25 ml egg-plant type flask was flushed with argon, and 42.4 mg (0.45 mmol) of phenol, 2 ml of dry 1,1,2-trichloroethane and 95.3 mg (0.45 mmol) of N-fluoro-2-chloropyridinium-6-sulfonate were charged. The flask was immersed in an oil bath of 100° C. and heated for 49 hours. After completion of the reaction, the reaction solution was washed with water to remove 2-chloropyridine-6-sulfonic acid. The organic layer was quantitatively analyzed by gas chromatography. o-Fluorophenol was obtained at a conversion yield of 58%, and phenol was recovered at a recovery rate of 5%.

REFERENCE EXAMPLE 4

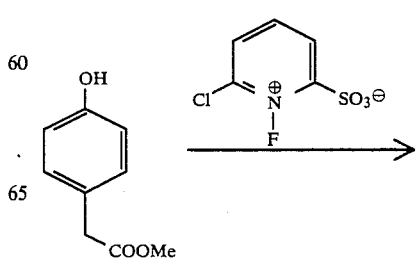

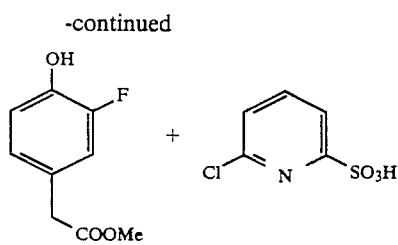 + 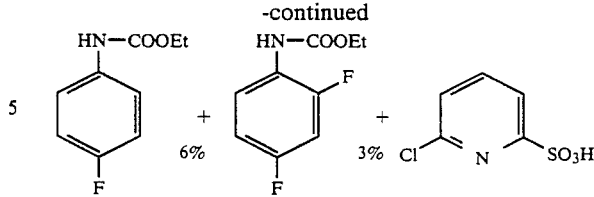

A 25 ml egg-plant type flask was flushed with argon, and 83.0 mg (0.5 mmol) of methyl 4-hydroxyphenylacetate, 2 ml of dry 1,2-dichloroethane and 105.7 mg (0.5 mmol) of N-fluoro-2-chloropyridinium-6-sulfonate were charged. The flask was immersed in an oil bath of 80° C. and heated for 22 hours. After completion of the reaction, 20 ml of water was added thereto, and the mixture was extracted three times with 20 ml of methylene chloride. 2-Chloropyridine-6-sulfonic acid formed after the reaction was all transferred to the aqueous layer. The organic layer was washed with water and dried over anhydrous magnesium sulfate. Then, the solvent was distilled off under reduced pressure. The residue was purified by thin layer chromatography (eluent: hexane/diethyl ether=2/1) to obtain 49.4 mg (conversion yield: 63%) of methyl 3-fluoro-4-hydroxyphenylacetate, and 11.2 mg of methyl 4-hydroxyphenylacetate was recovered (recovery rate: 14%).

REFERENCE EXAMPLE 5

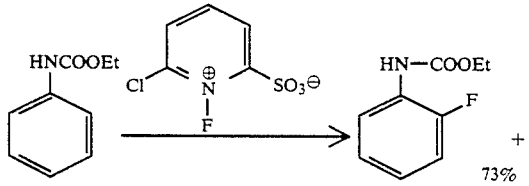

A 25 ml egg-plant type flask was flushed with argon, and 85.9 mg (0.52 mmol) of phenylurethane, 2 ml of dry 1,2-dichloroethane and 110.2 mg (0.52 mmol) of N-fluoro-2-chloropyridinium-6-sulfonate were charged. The flask was immersed in an oil bath of 80° C. and heated for 72 hours. Then, 20 ml of water was added thereto, and the mixture was extracted with methylene chloride (20 ml×3 times). 2-Chloropyridine-6-sulfonic acid formed after the reaction was all transferred to the aqueous layer. The organic layer was washed with water and dried over anhydrous magnesium sulfate. Then, the solvent was removed under reduced pressure. The residue was purified by thin layer chromatography (eluent: hexane/ethyl acetate=9/1) to obtain 58.6 mg (conversion yield: 73%) of 2-fluorophenylurethane, 4.9 mg (conversion yield: 6%) of 4-fluorophenylurethane and 2.8 mg (conversion yield: 3%) of 2,4-difluorophenyl-urethane. 14.1 mg of phenylurethane was recovered (recovery rate: 16%).

I claim:

1. A 2-halopyridine-6-sulfonic acid and its salt represented by the formula:

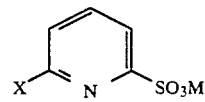

wherein X is a halogen atom, and M is a hydrogen atom or a metal atom.

2. Sodium 2-chloropyridine-6-sulfonate according to claim 1.

3. Potassium 2-chloropyridine-6-sulfonate according to claim 1.

4. 2-Chloropyridine-6-sulfonic acid according to claim 1.

5. Lithium 2-chloropyridine-6-sulfonate according to claim 1.

6. Sodium 2-fluoropyridine-6-sulfonate according to claim 1.

* * * * *